United States Patent [19]

Hsu et al.

[11] Patent Number: 4,714,770

[45] Date of Patent: Dec. 22, 1987

[54] DYE SILANE COMPOSITIONS

[75] Inventors: Li-Chien Hsu, Mission Viejo; Hal Heitzmann, Irvine, both of Calif.

[73] Assignee: Baxter Travenol Laboratories, Inc., Deerfield, Ill.

[21] Appl. No.: 537

[22] Filed: Jan. 5, 1987

[51] Int. Cl.[4] .......................... C07F 7/08; C07F 7/10; C07F 7/12
[52] U.S. Cl. ...................................... 556/419; 528/43; 528/34; 8/523; 8/581; 8/632; 8/648
[58] Field of Search ......................... 8/523, 632, 581; 556/419; 528/43, 34

[56] References Cited

U.S. PATENT DOCUMENTS

| | | | |
|---|---|---|---|
| 4,506,058 | 3/1985 | Ashby | 524/730 |
| 4,560,679 | 12/1985 | Toyoshima | 514/63 |
| 4,613,667 | 9/1986 | Marraccini | 546/14 |

*Primary Examiner*—Paul Lieberman
*Assistant Examiner*—Isabelle Rodriquez
*Attorney, Agent, or Firm*—Perman & Green

[57] ABSTRACT

The preparation of dye-silane compositions are disclosed. A dye-silane compound is formed in which the dye is covalently bonded to a cyano silane compound. These dye-silane polymer compositions have particular utility as dye adduct reactants in the preparation of dye containing polysiloxanes.

9 Claims, No Drawings

DYE SILANE COMPOSITIONS

BACKGROUND OF THE INVENTION

The present invention relates to the preparation of photoactive dye containing silane compounds. In particular, the present invention is directed to specific dye-silane compounds in which the dye is present in non-diffusible form thereby rendering these compounds particularly useful in the preparation of certain biological indicator systems.

The development of glass or plastic fibers, a fraction of a millimeter in diameter, for in vivo biomedical measurements, is a relatively new and important endeavor. Fiber-optic sensors can be as small as electrosensors and offer several distinct advantages. They are safe, involving no electrical connection to the body; the optical leads, very small and flexible, can be included in catheters for multiple sensing; and materials suitable for long term body implantation such as plastics, may be used.

The mechanism of fiber-optic sensor operation is relatively simple. Light from a suitable source travels along an optically conducting fiber to a receptor terminal where reflection, scattering or luminescence occurs. The affected light is then returned to a light meaurement instrument which interprets the returned signal. The light emanating from the sensing end of the fiber may be reflected by a tiny transducer that varies the reflectance with some parameter of interest, the light may be back scattered by the medium into which the fiber is inserted, or the returned light may be engendered from luminescence of something at the end of the fiber that was energized by the illuminating light. Of these three general types of in-vivo fiber-optic sensing mechanisms, the luminescence technique has been recently developed as a measurement to determine the amounts of gasses in blood.

Peterson et al in U.S. Pat. No. 4,200,100 developed a pH sensor as a biological in vivo device for determination of blood gasses. The pH sensor is based on classical acid-base dye indicator chemistry, with a miniature spectrophotometric cell at the end of a pair of optic fibers. In the cell, the dye indicator is covalently bonded to polyacrylamide microspheres so that the terminal is non diffusible and the sensor reusable. The dye-acrylic polymer composition offers a dye which is present in non-diffusible form but the hydrophilic polymer must be produced in the form of gas permeable microspheres in order to be used as the spectrophotometric cell of an optic fiber sensor.

The presence of unusually high or low oxygen content in blood samples may indicate various abnormalities. Peterson et al in U.S. Pat. No. 4,476,870 developed an optical sensor for measuring physiological oxygen gas, $PO_2$. The device is based on the quenching of the fluorescence of certain dyes by oxygen gas. Dyes are chosen for visible light excitation and are distributed on an adsorptive support medium for use as the light scattering terminal for the ingress and egress optical fiber waves. Generally, an inorganic gas adsorbant, such as silica gel, is used in the dye support medium. However, it has been found that such adsorbant materials are humidity-sensitive, thereby seriously interfering with fluorescence at high humidity.

While the $PO_2$ and pH probes of Peterson are effective the sensors suffer two disadvantages. First the indicator on both the PH and $PO_2$ probe is a two piece structure comprising a micro porous gas permeable envelope which houses a porous packing on which a dye is either adsorbed or chemically attached. Secondly, the two part indicator system requires a careful selection of materials and renders manufacturing more difficult.

Because of the importance of fiber-optic gas detecting chemical sensors, a need exists to develop or find materials which can act as molecular support mediums for dyes which can be used effectively and efficiently in the indicator portions of fiber optic sensors. It has been found that chemically attaching dyes to certain silane compounds provides photoactive center materials which readily react with certain gas permeable silicone polymers to form non diffusable dye indicator compositions.

OBJECTS OF THE INVENTION

It is therefore an object of this invention to provide novel fluorescent dye containing silane compositions.

It is a further object of this invention to provide a method for preparing novel polynuclear aromatic hydrocarbon based fluorescent dye containing silanes by reacting an organo functional/silicone functional silane with certain polynuclear aromatic compounds.

It is still a further object of this invention to provide fluorescent-silane compositions for use in preparing fiber-optic biological sensor devices.

SUMMARY OF THE INVENTION

In accordance with the present invention, there is provided a fluorescent-silane composition having particular compatibility and reactivity with silicone polymer compositions to faciliate the preparation of non-diffusible dye polymer compositions. The novel dye containing silanes are prepared by utilizing a unique organo functional/silicone functional silane coupling agent to effect chemical linkage between the polynuclear aromatic hydrocarbon dye and the silane.

By the present invention there is provided a method for the preparation of a dye-silane composition, in which the dye is chemically bonded to the silane through a urethane linkage. The resulting dye-silane adduct is a highly reactive compound with polysiloxane compositions to form dye substituted polysiloxanes such as those outlined in copending patent application, Ser. No. 000,529. The dye adducts of the present invention enable the expeditious preparation of elastomeric dye containing polymer compositions which can be used as a unitary non-diffusible indicator element in fiber optic biological probes.

DETAILED DESCRIPTION OF THE INVENTION

The fluorescent dye containing compounds of the present invention comprise silanes having the formula:

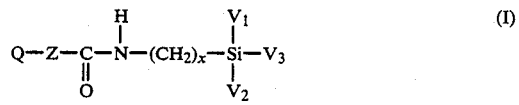

(I)

Where Q is a polynuclear aromatic hydrocarbon based fluorescent dye; x is an integer of from 1 to 10; Z is a hydrocarbon of up to 50 carbon atoms; and $V_1$, $V_2$ and $V_3$ are independently any hydrocarbon of up to 50 carbon atoms or a silicone polymer reactive substituent selected from the group comprising of hydrogen, halogen, alkenyl, acyloxy, alkoxy, amine or amide, with the proviso that at least one of the $V_1$, $V_2$, or $V_3$ substituents be a silicone reactive moiety.

Illustrative of the polynuclear aromatic hydrocarbon based fluorescent dye substituents, Q, used within the purview of the present invention are those of the pyrene, perylene, and benzoperylene family of dyes, having the following structural formulas:

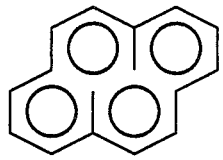

(II)

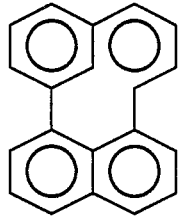

(III)

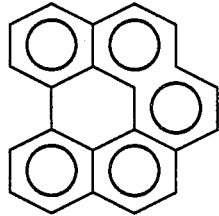

(IV)

The fluorescent dye-silane compositions of the present invention can be conveniently prepared by reacting a substituted polynuclear aromatic fluorescent dyes of the formula:

 (V)

wherein Q is polynuclear aromatic hydrocarbon based fluorescent dye, Z is any hydrocarbon substituent of up to 50 carbon atoms, and M is an isocyanate reactive substituent selected from the group comprising hydroxyl, carboxyl, amine and amide groups; with an organo functional/silicone functional silane having the formula:

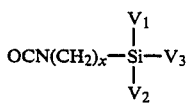 (VI)

where $V_1$, $V_2$ and $V_3$ are the same as defined above. The isocyanate radical of the silane is reactive with the isocyanate reactive group of the fluorescent dye.

An exemplary preparation of the instant dyes involves reacting 3-isocyanate-propyl dimethyl chlorosilane having the formula:

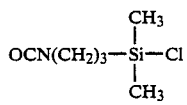

with an alkyl hydroxy substituted polynuclear aromatic fluorescent compound such as pyrene butanol having the following formula:

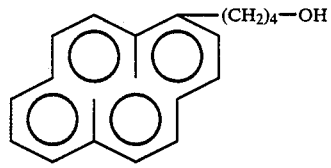

The reaction yields a pyrene silane adduct conforming to formula I.

The organo functional/silicone functional silane used within the purview of the present invention is that silane of the formula described above in VI wherein at least one of the V groups must be a silicone polymer reactive substituent such as hydrogen, halogen, alkenyl, acyloxy, alkoxy, amine or amide.

The pyrene, perylene and benzoperylene polynuclear aromatic fluorescent dyes illustrated in formulas III, IV, and V are oxygen quenching materials. However any dyes may be used within the spirit and scope of the present invention. In the bivalent side chain shown in the formula V dyes, Z can be any hydrocarbon of up to 20 carbon atoms. Illustrative polynuclear dye reactants include the hydroxyl and carboxylic acid derivatives of pyrene, perylene and benzoperylene.

The method of the present invention is performed by techniques typically used with silane compounds. In one embodiment, an isocyanate reactive aliphatic substituted polynuclear aromatic fluorescent dye is dissolved along with the difunctional isocyanate silane and a catalyst in an appropriate solvent. The substitution takes place and the fluorescent dye-substituted silane is recovered. Catalysts well known to those skilled in silicone chemistry may be used, typical ones being tin octoate, zinc octoate, and dibutyl tin dilaurate.

The silane-dye adducts of this invention are useful in a variety of applications for which dyes are conventionally employed. However, as discussed above, a particularly preferred and desired use for these compounds is as reactants with siloxane homopolymers and copolymers to form dye substituted polysiloxanes. These polymers are described in copending application Ser. No. 000,529 wherein the polymers are used in the indicator portion of fiber-optic chemical sensors, especially fiber-optic $PO_2$ probes as described in U.S. Pat. No. 4,476,870 to Peterson.

The dye substituted silane adducts of the present invention have particular utility because of their reactivity with vulcanizable silicone systems. Consequently the addition of the instant dye adducts to one or two part elastomeric silicone compositions results in a dye substituted elastomer which can be applied to the terminals of a pair of optically active terminals to readily cure as a solid gas permeable integral indicator medium for a sensor probe.

While not to be construed as limiting, the reactivity of the present adducts with polysiloxanes is due to the selection of a silicone polymer reactive substitute on at least one of the functional groups $V_1$, $V_2$ or $V_3$, in the silane molecule. As an example, such a group would react readily with hydroxyl groups on a silanol terminated siloxane polymer thereby bonding the dye adduct directly to the siloxane polymer backbone, as illustrated as follows for a silicone polymer reactive carboxylate group

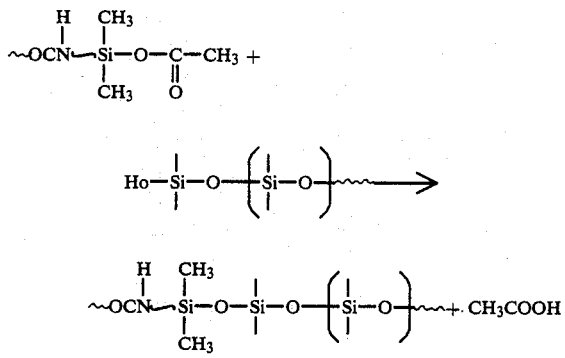

The following examples are included for further understanding of the invention. It should be understood that these examples are in no way intended to limit the scope of the present invention.

EXAMPLE I

The following example illustrates the preparation of a dye-silane adduct of the present invention. The molar ratio of pyrene butanol to isocyantopropylchlorosilane was 1 to 20. Tin Octoate was used as the catalyst at a 0.1% level (weight of catalyst to weight of reactants).

Pyrene butanol was dissolved in methylene chloride (about 0.4% w/v). The catalyst, tin octoate, was then added, while stirring. Minor amounts of isocyantopropylchlorosilane at small increments was added to the solution over a period of 30 minutes. A significant increase in molecular weight was observed after the mixture was agitated at room temperature for one hour. A Gel Permeation Chromatographic Analysis (GPC) demonstrated the molecular weight increase which indicated that a new and a higher molecular weight substance had been formed.

EXAMPLE II

The following illustrates the use of the dye-isocyanosilane adduct of Example I in one-part room temperature vulcanizable silicone systems and the preparation of an optical sensor device.

The fluorescent dye/isocyanosilane adduct prepared in Example I is blended into a one part moisture cured silicone elastoner containing acetoxy terminated polydimethylsiloxane. When the blend was cured it was found that the dye/silane adduct had reacted with the hydroxyl end groups of the polydimethylsiloxane to form a dye containing polydimethyl siloxane. Before the blend was cured a fiber optical probe was dipped and allowed to cure thereby forming an integral indicator terminal for the two strobe strands. The optically active probe was subjected to a favorable leachability test as outlined in copending application, Ser. No. 000,529 which indicated the chemical bonding of the pyrene butanol to the silicone polymer.

EXAMPLE III

The following illustrates the use of the dye-isocyanosilane adduct of Example I in a two part room temperature vulcanizable silicone system.

The dye/isocyano silane adduct prepared in Example I is blended into a two part room temperature vulcanizable elastomer comprising silanol terminated polydimethylsiloxane as the matrix backbone, triethoxysilane as the crosslinker and tin octoate as the catalyst. Upon curing there results a crosslinked branched polysiloxane in which the pyrene butanol molecule is chemically bonded to the silicone resin network. This optically active probe was also subjected to a favorable leachability test as outlined in copending application Ser. No. 000,529 which again indicates the chemical bonding of the dye aduct to the silicone polymer.

Although variations are shown in the present application, many modifications and ramifications will occur to those skilled in the art upon a reading of the present disclosure. These, too, are intended to be included herein.

What is claimed:

1. A dye containing silicon composition having the formula

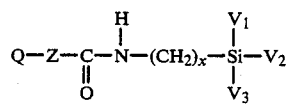

wherein Q is a polynuclear aromatic hydrocarbon based fluorescent dye; "selected from the group of polynuclear aromatic dyes consisting of pyrene, perylene, benzopylene and derivatives thereof" X is an integer of from 1 ro 50. Z is a hydrocarbon of up to 50 carbon atoms; and $V_1$, $V_2$, and $V_3$ are independently any hydrocarbon of up to 50 carbon atoms or hydrogen, halogen, alkenyl, acyloxy, alkoxy, amine or amide, with the proviso that at least one of the $V_1$, $V_2$, or $V_3$ substituents be a "hydrogen, halogen, alkenyl, acyloxy, alkoxy, amine or amide." derivatives thereof.

2. The composition of claim 1 wherein $V_1$, $V_2$ and $V_3$ is a halogen selected from the group comprising fluorine, chlorine, bromine and iodine.

3. The composition of claim 1 wherein x is 3 and Q is a pyrene substituent.

4. A method of preparing a dye-silane composition comprising reacting a substituted polynuclear aromatic hydrocarbon based fluorescent dye of the formula:

Q—Z—M wherein Q is a polynuclear aromatic hydrocarbon based fluorescent dye moiety, Z is a hydrocarbon of up to 50 carbon atoms, and M is an isocyanate reactive substituent selected from the group comprising hydroxyl, carboxyl, amine, and amide groups; with an organo functional/silicone functional silane having the formula:

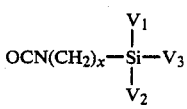

wherein X is an integer of from 1 to 10; and $V_1$, $V_2$, and $V_3$ are independently any hydrocarbon of up to 50 carbon atoms or a silicone polymer reactive substituent group selected from the group comprising hydrogen, halogen, alkenyl, acyloxy, alkoxy, amine or amide, with the proviso that at least one of the $V_1$, $V_2$ or $V_3$ substituents be a silicone reactive moiety.

5. The method of claim 4 wherein the polynuclear aromatic fluorescent dye moiety is selected from a group comprising pyrene, perylene, benzoperylene, and derivatives thereof.

6. The method of claim 5 wherein Z is a straight chain aliphatic group containing up to 20 carbon atoms and M is hydroxyl.

7. The method of claim 6 wherein the reaction is carried out in the presence of a catalyst selected from the group consisting essentially of tin octoate, zinc octoate, and dibutyl tin dilaurate.

8. The method of claim 7 wherein the organo functional/silicone functional silane is isocyanopropylsilane.

9. The method of claim 8 wherein the dye reactant is pyrene butanol.

* * * * *